United States Patent [19]

Gallina

[11] Patent Number: 5,234,914
[45] Date of Patent: Aug. 10, 1993

[54] METHODS OF TREATING HEMORRHOIDS AND ANORECIAL DISEASE

[75] Inventor: Damian J. Gallina, Erie, Pa.
[73] Assignee: Patent Biopharmaceutics, Inc., Erie, Pa.
[21] Appl. No.: 799,751
[22] Filed: Nov. 27, 1991

Related U.S. Application Data

[63] Continuation-in-part of Ser. No. 712,880, Jun. 11, 1991, abandoned.
[51] Int. Cl.$^5$ .................... C07M 1/00; A61K 31/715; A61K 9/02; A61K 35/44
[52] U.S. Cl. ...................................... 514/54; 514/882; 514/966; 514/912; 514/944; 536/55.1; 536/55.3; 536/18.7; 536/54; 424/489
[58] Field of Search ................. 514/54, 882, 966, 912, 514/944; 536/18.7, 55.3, 54, 53, 55.1; 424/489, 15

[56] References Cited

U.S. PATENT DOCUMENTS

| | | | |
|---|---|---|---|
| 1,525,505 | 2/1925 | Kavanagh | 424/DIG. 15 |
| 2,583,096 | 1/1952 | Hadidian et al. | 514/54 |
| 2,850,428 | 9/1958 | Seifter et al. | 514/54 |
| 3,103,466 | 9/1963 | Farkas | 514/54 |
| 3,159,539 | 12/1964 | Mendelsohn | 514/54 |
| 3,396,081 | 8/1968 | Billek | 536/55.1 |
| 3,594,473 | 7/1971 | Hunger et al. | 514/54 |
| 3,792,164 | 2/1974 | Bechtold | 514/54 |
| 3,845,201 | 10/1974 | Haddad et al. | 424/22 |
| 3,870,791 | 3/1975 | Haddad et al. | 514/54 |
| 3,887,703 | 6/1975 | Manoussos et al. | 514/54 |
| 4,105,760 | 8/1978 | Szejtli et al. | 536/54 |
| 4,141,973 | 2/1979 | Balazs | 514/54 |
| 4,156,719 | 5/1979 | Sezaki et al. | 424/118 |
| 4,303,676 | 12/1981 | Balazs | 424/359 |
| 4,328,803 | 5/1982 | Pape | 514/54 |
| 4,359,458 | 11/1982 | Nair | 536/55 |
| 4,486,416 | 12/1984 | Soll et al. | 514/54 |
| 4,514,384 | 4/1985 | Gallina | 514/882 |
| 4,517,295 | 5/1985 | Bracke et al. | 514/54 |
| 4,518,583 | 5/1985 | Gallina | 514/882 |
| 4,563,182 | 1/1986 | Stoy et al. | 424/DIG. 15 |
| 4,582,865 | 4/1986 | Balazs et al. | 536/4.1 |
| 4,629,623 | 12/1986 | Balazs et al. | 514/912 |
| 4,678,516 | 7/1987 | Alderman et al. | 424/DIG. 15 |
| 4,698,359 | 10/1987 | Niederer et al. | 514/966 |
| 4,703,108 | 10/1987 | Silver et al. | 514/801 |
| 4,707,360 | 11/1987 | Brasey | 424/DIG. 15 |
| 4,711,780 | 12/1987 | Fahim | 514/562 |
| 4,716,154 | 12/1987 | Mälson et al. | 514/54 |
| 4,716,224 | 12/1987 | Sakurai et al. | 536/55.1 |
| 4,725,585 | 2/1988 | Wenge et al. | 514/54 |
| 4,736,024 | 4/1988 | Della Valle et al. | 536/55.3 |
| 4,746,504 | 5/1988 | Nimrod et al. | 514/54 |
| 4,761,401 | 8/1988 | Couchman et al. | 514/53 |
| 4,772,419 | 9/1988 | Mälson et al. | 536/55.1 |
| 4,782,046 | 11/1988 | Brown et al. | 514/54 |
| 4,784,990 | 11/1988 | Nimrod et al. | 514/54 |
| 4,784,991 | 11/1988 | Nimrod et al. | 514/21 |
| 4,795,741 | 1/1989 | Leshchiner et al. | 514/21 |
| 4,801,619 | 1/1989 | Lindblad | 514/54 |
| 4,808,576 | 2/1989 | Schultz et al. | 514/54 |
| 4,818,538 | 4/1989 | Rideout et al. | 514/966 |
| 4,820,516 | 4/1989 | Sawyer et al. | 514/912 |
| 4,851,521 | 7/1989 | della Valle et al. | 536/55.1 |
| 4,879,375 | 11/1989 | Cullis et al. | 536/55.1 |
| 4,885,244 | 12/1989 | Miyamori et al. | 536/55.1 |
| 4,920,104 | 4/1990 | DeVore et al. | 514/54 |
| 4,937,270 | 6/1990 | Hamilton et al. | 514/777 |
| 4,957,744 | 9/1990 | della Valle et al. | 514/54 |
| 4,965,253 | 10/1990 | Goldberg et al. | 514/54 |
| 4,965,353 | 10/1990 | della Valle et al. | 514/54 |
| 4,973,580 | 11/1990 | Mascellani et al. | 514/54 |
| 4,981,841 | 1/1991 | Gibson | 514/54 |
| 4,983,580 | 1/1991 | Gibson | 514/54 |
| 5,008,102 | 4/1991 | York | 424/59 |
| 5,008,253 | 4/1991 | Casu et al. | 514/54 |
| 5,017,229 | 5/1991 | Burns et al. | 514/777 |
| 5,028,597 | 7/1991 | Kodama et al. | 514/56 |

FOREIGN PATENT DOCUMENTS 56-138110 10/1981 Japan .

OTHER PUBLICATIONS

The Merck Index, 11th ed. (1989), pp. 751-752 and 1513.

Primary Examiner—Ronald W. Griffin
Assistant Examiner—Louis N. Leary
Attorney, Agent, or Firm—Cushman, Darby & Cushman

[57] ABSTRACT

A method of treating hemorrhoids and anorectal disease which includes applying to the hemorrhoids and anorectal tissues an effective amount of a composition including a pharmaceutically acceptable carrier and hyaluronic acid or pharmaceutically acceptable salts thereof.

11 Claims, No Drawings

METHODS OF TREATING HEMORRHOIDS AND ANORECIAL DISEASE

This is a continuation-in-part of application Ser. No. 07/712,880, filed on Jun. 11, 1991, which was abandoned.

BACKGROUND OF THE INVENTION

The present invention relates to methods of treating hemorrhoids and diseases of the anorectum employing novel pharmaceutical compositions. In particular, the present invention relates to topical applications of hyaluronate preparations as rectal bonding and adhesion agents, anti-inflammatory agents and bio-repair materials. The use of hyaluronate preparations employs their properties to reduce the inflammation, pain, swelling, and sequelae of injured, irritated, diseased, strained, or traumatized anorectal tissues while adhering to and protecting sensitive tissues of the anorectum. The source of the hyaluronate used in the treatment compositions may be a hyaluronic acid or any acceptable salt form of hyaluronic acid. The term "hyaluronate" is often used to mean "hyaluronic acid equivalent" which equates to hyaluronic acid of varying molecular weights and any of their salt forms.

Hyaluronic acid is a naturally occurring mucopolysaccharide with a molecular weight generally ranging between about 50,000 and 8,000,000 (or possibly higher), depending on the sources of the hyaluronate and the analytical methods used in its determination.

Methods of obtaining highly-pure or ultra-pure hyaluronic acid and its salt forms, isolation techniques, and analytical methods for testing purity are provided, for example, in the U.S. Pat. Nos. 3,396,081, 4,141,973, 4,517,295, 4,736,024, 4,784,990 and 4,808,576.

Hyaluronic acid is well known, being found in the joint tissue and vitreous humor of the eyes of mammals. It has been extracted from rooster combs, human umbilical cords and bacterial cultures such as those of hemolytic group A and C streptococci for various therapeutic purposes. One of the first therapeutic uses of this material was as a replacement for the liquid vitreous of the human eye to aid in ophthalmic surgery, especially in the treatment of retinal detachment. It has also been used for the relief of trauma or irritation in joint tissue of mammals including humans by injection into the synovial fluid of the joint.

An extensive discussion of its various uses is found in U.S. Pat. No. 4,141,973. The administration of hyaluronic acid alone and with cortisone in various animal joints, especially horses, is discussed in the article by Rydell et al., "Effect of Intra-articular Injection of Hyaluronic Acid on the Clinical Symptoms of Osteoarthritis and on Granulation Tissue Formation", *Clinical Orthopaedics and Related Research*, October, 1971, No. 80. The use of hyaluronic acid in human joints is reported in the "Preliminary Clinical Assessment of Na Hyaluronate Injection into Human Arthritic Joints" by Peyron et al., *Pathologic Biologic*, October, 1974, Vol. 22, No. 8. The use of hyaluronic acid in reducing fibrotic wound reactions is reported in the article by Rydell, "Decreased Granulation Tissue Reaction After Installment of Hyaluronic Acid", *Acta Orthop. Scandinav*, Vol. 41.

Hyaluronic acid and derivatives thereof can play a critical role in wound healing. Hyaluronate preparations are already marketed by several companies as products utilized in eye surgery, hip repair, dentistry, cosmetics, skin treatments, and dermatology.

U.S. Pat. No. 4,736,024 describes the use of hyaluronic acid or a molecular weight fraction thereof as a vehicle for pharmacologically active substances. The vehicle may be in suppository form for transcutaneous absorption to obtain a systemic effect. In contrast, the present methods of treatment employ the bonding, protective, healing, therapeutic, and curative properties of hyaluronic acid and derivatives thereof for their direct, local therapeutic affect when applied topically to thrombosed anorectal vessels, inflamed tissues of the anorectum, rectal fissures, and/or pruritis ani. In the present invention, hyaluronic acid (and its derivatives) is the active pharmaceutical agent.

For the present invention, pharmaceutical preparations containing less than 0.1% to more than 25.0% hyaluronate have been made and applied topically to the anorectum in successfully relieving the tenderness, soreness, pain, burn, itch, and discomfort of inflamed, irritated anorectal tissues. Hyaluronate reduces pain, inflammation, and swelling due to its anti-inflammatory and membrane stabilizing properties. Hyaluronate protects sensitive tissues and vessels of the anorectal epithelium and rectal mucosa by adhering to them and can remarkably mask the trauma of inflamed tissues.

SUMMARY OF THE INVENTION

The present invention relates to a method of treating hemorrhoids and other anorectal diseases by topically applying to hemorrhoidal and anorectal tissues a pharmaceutical preparation comprising a hyaluronate acid moiety such as hyaluronic acid or an acceptable salt form of hyaluronic acid, in an effective amount for the treatment of anorectal disease. The disease states of the anorectum include but are not limited to hemorrhoids, rectal fissures, inflamed anorectal tissues, pruritis ani and proctitis.

It is accordingly one important object of the present invention to provide a method for promoting the healing of traumatized, injured, irritated, inflamed, or diseased anorectal tissues while reducing the pain, burn, inflammation, itch, and swelling of these tissues by means of the topical application of a hyaluronate preparation. The hyaluronate preparation displays a powerful anti-inflammatory action on anorectal tissues.

An important advantage of using hyaluronate for anorectal treatment is that while sodium hyaluronate, for example, may be compared to hydrocortisone in its anti-inflammatory affect, unlike hydrocortisone or other glucocorticoids, sodium hyaluronate is not catabolic in nature. Hyaluronic acid and its derivatives stabilize cellular membranes, reduce inflammation and enhance the anabolic process as opposed to the catabolic process.

It is a related object of the present invention to provide an improved method of treating hemorrhoids and other anorectal problems by utilizing the advantageous bonding and adhering properties as well as the anti-inflammatory and healing properties of hyaluronic acid and its various salt forms.

DETAILED DESCRIPTION OF THE PREFERRED EMBODIMENTS

Pain, discomfort, tenderness, inflammation, and swelling are reduced when hyaluronic acid or an acceptable salt form of hyaluronic acid are applied directly to irritated, inflamed, traumatized, strained, or injured tissues of the anorectum. One embodiment of the present invention is the use of hyaluronate in the treatment of hemorrhoidal and other anorectal disease conditions employing the anti-inflammatory property of hyaluronic acid and its derivatives.

Another embodiment of the present invention is to employ the property of hyaluronic acid and its derivatives to bond or strongly adhere to tissues of the anorectum in methods of treatment, which provides a protective coating on irritated, inflamed, sore, tender, and sensitive anorectal tissues, such as hemorrhoids.

A further embodiment of the present invention is to employ the property of hyaluronic acid and its derivatives to promote the healing of injured, irritated, strained, diseased or traumatized anorectal tissues.

Additional embodiments of the present invention include: (1) treatment of internal and external hemorrhoids; (2) treatment of inflamed anorectal tissues; (3) treatment of rectal fissures; (4) treatment of pruritis ani; and (5) treatment of proctitis.

Any pharmaceutically acceptable form of hyaluronic acid may be used in the present invention. This application will for the most part, however, be principally concerned with the representative use of the readily available commercial forms of hyaluronate, such as hyaluronic acid, the potassium salt of hyaluronic acid, and more preferably sodium hyaluronate. This in no way limits the forms of hyaluronic acid employed in the present invention Hyaluronic acid and derivatives thereof may be incorporated into numerous types of gels, creams, ointments, lotions, pastes, salves, liquids, and/or solid suppository vehicles. Sterile distilled water alone and simple cream, ointment and suppository bases may be employed as carriers of the hyaluronic acid and derivatives. Examples of suppository bases and suspending vehicles include Fattibase TM (polyethylene glycol base), Vehicle-S TM (acrylic polymer resin base), and Polybase TM (polyethylene glycol base) by Paddock Laboratories, Inc., Minneapolis, Minn. Such pharmaceutically acceptable carriers are readily available for preparing the present formulations and have desirable pH's, melting points, and preservatives.

In its more specific aspects, the preferred concentration of hyaluronate in the treatment formulation ranges from about 0.01% to 25 0% by weight and more preferably from about 0.1% to 20.0% by weight and most preferably from about 1.0% to 10.0% by weight.

Additional therapeutic agents may be added to the present formulations as medically indicated, selected from the classes of: keratolytics, surfactants, counterirritants, humectants, antiseptics, lubricants, astringents, wound healing agents, emollients, additional adhesion/coating protectants, additional anti-inflammatory agents, vasoconstrictors, anticholinergics, corticosteroids (e.g. glucocorticoids) and anesthetics. Preservatives and buffers may also be added.

The invention is further illustrated by the following examples:

EXAMPLES

Exemplary Hyaluronate Preparations of the Present Invention

The present hyaluronate preparations may be formulated as a solid, gel, paste, cream, salve, lotion, liquid, ointment, and powder, depending on the ingredients and the amounts used.

Example A) Twelve (12) suppositories were prepared containing 0.5% sodium hyaluronate assuming the average weight of the suppository to be 2.0 gm and allowing for a 10% overfill and shrinkage:

1. Melt 26.268 gm of Polybase TM, a preblended suppository base consisting of a homogenous mixture of various molecular weight polyethylene glycols with a specific gravity of 1.777 at 25° C., in a pyrex beaker over a hot plate or water bath;
2. add 0.132 gm of finely powdered sodium hyaluronate to the heated Polybase TM with continuous agitation;
3. pour into suppository mold and chill; and
4. trim excess with razor blade or spatula.

Calculations:   26.268 gm Polybase TM
              + 0.132 gm Sodium Hyaluronate
              = 26.400 gm Total Blend One suppository = 2.0 gm Each suppository contains 0.5% (10 mg) sodium hyaluronate. A total of 12 suppositories were prepared.

Example B) Twelve (12) suppositories were prepared containing 1% sodium hyaluronate and 1% hydrocortisone, following the procedure described in Example A:

1. melt 25.872 gm Polybase TM;
2. add 0.264 gm Sodium Hyaluronate;
3. add 0.264 gm Hydrocortisone; and
4. repeat steps 3 and 4 of Example A.

Calculations:   25.872 gm Polybase TM
              + 0.264 gm Sodium Hyaluronate
              + 0.264 gm Hydrocortisone
              = 26.400 gm Total Blend One suppository = 2.0 gm Each suppository contains 1% (20 mg) of sodium hyaluronate and 1% (20 mg) of hydrocortisone. A total of 12 suppositories were prepared.

Example C) A 100 gm sample of a 2½% sodium hyaluronate cream based formulation was prepared containing the following components:

| | |
|---|---|
| 12.0 gm | Sterile H$_2$O |
| 5.5 gm | Propylene glycol |
| 15.0 gm | Polyethylene glycol-400 |
| 2.5 gm | Sodium Hyaluronate |
| 6.0 gm | Vehicle-S TM, a preblended aqueous vehicle containing carboxypolymethylene, polysorbate 80, simethicone and methylparaben, 0.18% as a preservative. |
| 9.0 g | Polyethylene glycol-8000 (melt) |
| 30.0 gm | Polybase TM (melt) |
| 20.0 gm | Fattibase TM (melt), a prebended base consisting of a homogenous mixture of triglycerides from coconut, palm and palm kernel oils. |
| 100.0 gm | Total |

Example D) A 2% sodium hyaluronate cream based formulation containing 1% hydrocortisone and 1% pramoxine HCL was prepared containing the following components:

| | |
|---|---|
| 14.0 gm | Sterile H$_2$O |
| 6.0 gm | Propylene glycol |
| 13.0 gm | Polyethylene glycol-400 |
| 2.0 gm | Sodium Hyaluronate |
| 1.0 gm | Hydrocortisone |
| 1.0 gm | Pramoxine HCL |

-continued

| | |
|---|---|
| 7.0 gm | Vehicle-S ™ |
| 9.0 gm | polyethylene glycol-8000 |
| 27.0 gm | Polybase ™ |
| 27.0 gm | Fattibase ™ |
| 100.0 gm | Total |

Example E) A 7% hyaluronate cream based formulation containing 5% Lidocaine HCL was prepared containing the following components:

| | |
|---|---|
| 15.0 gm | Sterile H₂O |
| 5.0 gm | Propylene glycol |
| 10.0 gm | Polyethylene glycol-400 |
| 7.0 gm | Sodium Hyaluronate |
| 5.0 gm | Lidocaine HCL |
| 6.0 gm | Vehicle-S ™ |
| 8.0 gm | Polyethylene glycol-8000 |
| 24.0 gm | Polybase ™ |
| 20.0 gm | Fattibase ™ |
| 100.0 gm | Total |

Example F) A 5% hyaluronate ointment containing 2% benzocaine was prepared containing the following components:

| | |
|---|---|
| 10 gm | Sterile H₂O |
| 7 gm | Propylene glycol |
| 15 gm | Polyethylene glycol-400 |
| 5 gm | Sodium Hyaluronate |
| 2 gm | Benzocaine |
| 8 gm | Vehicle-S ™ |
| 10 gm | Polyethylene glycol-8000 |
| 10 gm | Polybase ™ |
| 22 gm | Fattibase ™ |
| 11 gm | Aquaphor, a preblended cholesterolized anhydrous water miscible ointment base consisting of petrolatum, mineral oil, mineral wax, and woolwax alcohol. |
| 100 gm | Total |

Example G) Stable gel formulations of hyaluronate were prepared using only water as the vehicle, containing the components as respectively listed:

| | | |
|---|---|---|
| 1. 2.5% formulation = | 2.5 gm | Sodium Hyaluronate |
| | + 97.5 gm | Sterile H₂O (QS) |
| Total | 100.0 gm | of a 2.5% gel formulation. |
| 2. 5.0% formulation = | 5.0 gm | Sodium Hyaluronate |
| | + 95.0 gm | Sterile Water (QS) |
| Total | 100.0 gm | of a 5% gel formulation. |

Numerous formulations may be derived by varying the concentrations of the above mentioned ingredients of the above Examples and may be determined by the desired characteristics of the finished products. It should also be remembered that other vehicle systems are available for this purpose and therefore this disclosure is not limited to the examples given.

First Exemplary Clinical Evaluation

The effaciousness of the present methods of treating anorectal disease states was demonstrated by the following clinical evaluation:

a. Eighty individuals suffering from external and internal hemorrhoids and rectal fissures were selected for the study.

b. The patients were randomly divided into two groups: a control group and the test group.

c. The control group (40 patients) was subjected to standard medical treatment for external thrombosed hemorrhoids. This treatment entailed use of conventional sitz-baths, limited physical activity and conventional controlled diet (e.g. high fiber, low fat). The test group (40 patients) was subjected to the same treatment but also treated with a topical cream containing a specific concentration of sodium hyaluronate as the active ingredient. The three different concentrations of sodium hyaluronate used in this study were: 2.0%, 3.5% and 5.0%.

d. The hyaluronate preparations were topically applied 2–4 times daily via fingercots by each member of the test group.

e. After the initial consultation by the patients with the physician, a nurse contacted each patient by phone every day for one week for the purpose of monitoring each patient. Each patient visited and consulted with the rectal and colon surgeon-physician once a week for a total of five visits. One patient-physician visit/week multiplied by 5 weeks multiplied by 80 patients=400 patient-physician visits.

f. The following parameters were determined and statistically compared: (1) Pain-free time intervals; (2) reduction of swelling (resolving of thrombosed conditions; and (3) general improvement of the anorectum. Hypothesis testing was performed at the 5% significance level.

(i) 65.0% of the experimental group (26 patients) experienced pain free time intervals of 4 hours or longer following rectal application of a sodium hyaluronate preparation.

(ii) 20% of the control group (8 patients) reported pain free time intervals of one hour or longer following sitz bath treatment.

(iii) No member of the control group reported pain free time intervals greater that 2 hours following standard treatment methods only.

(iv) 80% of the control group (32 patients) experienced pain free time intervals of one hour or less following sitz bath treatment only.

(v) The experimental group reported less painful bowel movements when a sodium hyaluronate preparation was applied to the anorectal canal within one hour prior to defecation. There were no reported improvements in defecating in the control group following the standard treatment modalities.

g. This study conclusively proves the utility and benefit of using the present hyaluronate preparations in the methods of the present invention for treatment of anorectal disease conditions by relieving pain and enhancing healing of injured or diseased anorectal tissues.

Second Exemplary Clinical Evaluation

The efficaciousness of the present methods of treating anorectal disease states was again demonstrated by the following second clinical evaluation:

a. A 2% sodium hyaluronate cream based formulation was prepared containing the following components:

| | |
|---|---|
| 2% | Sodium hyaluronate |
| 1% | Benzyl alcohol |
| 1.5% | Sodium propionate |
| 2.25% | Fattibase ™ |
| 0.75% | Lecithin |

| | |
|---|---|
| 0.75% | Glycerin |
| 0.75% | Polyethylene glycol - 4000 |
| 91% | Sterile H₂O |
| 100% | | b. Twenty patients suffering from anorectal disorders were selected for the study. The disorders and number of patients having the disorders were as follows:
  8 patients had either perianal irritation or pruritis ani;
  4 patients had grade 1-2 bleeding hemorrhoids;
  4 patients had fissures (two chronic with sphincter spasm, one superficial and one with a large AIDS (Acquired Immune Deficiency Syndrome) ulceration);
  3 patients had prolapsing hemorrhoids; and
  1 patient had a thrombosed external hemorrhoid.

c. The 20 patients were supplied with 20 gram tubes containing the above 2% sodium hyaluronate preparation. Pile pipe rectal applicators were provided with the tubes for those patients requiring such applicators. The patients were instructed to topically apply the hyaluronate preparation three times each day, either digitally or by applicator as appropriate. The study period was two weeks.

d. The patients were initially observed by a physician. The patients were instructed to complete a questionnaire at the end of the two-week study period to determine whether the hyaluronate preparation was effective. The following parameters were determined for each patient:
  1) the effectiveness of the hyaluronate preparation after application, being rated as effective either a) every time, b) sometime or c) not at all; and
  2) the overall effectiveness of the hyaluronate preparation, being rated as a) excellent, b) good, c) fair or d) poor.

e. The results of the study showed that 18 of the 20 patients (90%) rated the hyaluronate preparation to be effective either every time (6 patients) or sometime (12 patients). These patients who rated the cream as effective in turn rated the preparation as excellent (6 patients), good (9 patients), and fair (3 patients). Thus, 75% of the patients rated the hyaluronate preparation as good or excellent.

(i) The hyaluronate preparation relieved symptoms of itching, burning, bleeding, irritation and pain, depending upon the anorectal disorder.

(ii) The two patients who rated the cream as ineffective had anorectal disorders resulting from mechanical type problems.

(iii) Significantly, the patient with the AIDS ulceration, which is typically a difficult problem to treat, found great relief by employing the hyaluronate preparation.

f. This study conclusively proves the utility and benefit of using the present hyaluronate preparations and the methods of the present invention for treatment of anorectal disease conditions by relieving pain and enhancing healing of injured or diseased anorectal tissues.

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

I claim:

1. A method of treating hemorrhoids and anorectal disease which comprises topically applying to the hemorrhoids and anorectal tissues in need of such treatment an effective amount of a composition comprising a pharmaceutically acceptable carrier and hyaluronic acid or pharmaceutically acceptable salts thereof, as the active ingredient in an amount of 0.1 to 10.0% by weight.

2. The method of claim 1 wherein said composition includes hyaluronic acid or a pharmaceutically acceptable salt thereof in an amount of 1.0-10.0% by weight.

3. The method of claim 1 wherein said composition further includes material selected from the group consisting of keratolytics, surfactants, counter-irritants, humectants, antiseptics, lubricants, astringents, emollients, wound healing agents, adhesion/coating protectants, vasoconstrictors, anticholinergics, corticosteroids, anesthetics and anti-inflammatory agents.

4. The method of claim 1 wherein said composition is in a form selected from the group consisting of gel, solid, paste, salve, lotion, liquid, cream, ointment and powder.

5. The method of claim 1 wherein said carrier is water.

6. A method of treating inflammation of anorectal tissues which comprises topically applying to anorectal tissues in need of such treatment an effective amount of a composition comprising a pharmaceutically acceptable carrier and hyaluronic acid or a pharmaceutically suitable salt thereof, as the active ingredient in an amount of 0.1 to 10.0% by weight.

7. A method of treatment for providing a protective coating on hemorrhoids and anorectal diseased tissues in need of such treatment which comprises topically applying an effective amount thereto of a composition comprising a pharmaceutically acceptable carrier and hyaluronic acid or a pharmaceutically acceptable salt thereof, as the active ingredient in an amount of 0.1 to 10.0% by weight.

8. A method of treatment by promoting healing of hemorrhoids and anorectal disease which comprises topically applying to hemorrhoids and anorectal tissues in need of such treatment an effective amount of a composition comprising a pharmaceutically acceptable carrier and hyaluronic acid or a pharmaceutically acceptable salt thereof, as the active ingredient in an amount of 0.1 to 10.0% by weight.

9. A method of treating rectal fissures which comprises topically applying to rectal tissues in need of such treatment an effective amount of a composition comprising a pharmaceutically acceptable carrier and hyaluronic acid or a pharmaceutically acceptable salt thereof, as the active ingredient in an amount of 0.1 to 10.0% by weight.

10. A method of treating pruritis ani which comprises topically applying to anorectal tissues in need of such treatment an effective amount of a composition comprising a pharmaceutically acceptable carrier and hyaluronic acid or a pharmaceutically acceptable salt thereof, as the active ingredient in an amount of 0.1 to 10.0% by weight.

11. A method of treating proctitis which comprises topically applying to anorectal tissues in need of such treatment an effective amount of a composition comprising a pharmaceutically acceptable carrier and hyaluronic acid or a pharmaceutically acceptable salt thereof, as the active ingredient in an amount of 0.1 to 10.0% by weight.

* * * * *

UNITED STATES PATENT AND TRADEMARK OFFICE
CERTIFICATE OF CORRECTION

PATENT NO. : 5,234,914
DATED : August 10, 1993
INVENTOR(S) : Gallina, Damian J.

It is certified that error appears in the above-indentified patent and that said Letters Patent is hereby corrected as shown below:

On the Title page, item [54], and col. 1, line 1-2, change "ANORECIAL" to --ANORECTAL--;

item [56], insert under OTHER PUBLICATIONS, after "The Merck Index" reference --Pulbication re: product "Connettivina" manufactured by Fidia Farmaceutici Italiani Derivati Industriali E Affini SP (34 pages) (probably published in early 1980's)--; and Correct the Assistant Examiner's name to read--Louise N. leary--.

Signed and Sealed this

Twenty-sixth Day of April, 1994

Attest:

BRUCE LEHMAN

*Attesting Officer*     Commissioner of Patents and Trademarks